US006030410A

United States Patent [19]
Zurbrügg

[11] Patent Number: 6,030,410
[45] Date of Patent: Feb. 29, 2000

[54] STERNAL CLOSURE TECHNIQUE AND KIT FOR PERFORMING SAME

[76] Inventor: Heinz Robert Zurbrügg, Bündackerstrasse 158, CH-3047 Bremgarten, Switzerland

[21] Appl. No.: 09/080,444

[22] Filed: May 18, 1998

[51] Int. Cl.⁷ .................................................. A61B 17/08
[52] U.S. Cl. ........................... 606/219; 606/151; 606/216
[58] Field of Search ................................. 606/151, 232, 606/219, 220, 216; 128/898

[56] References Cited

U.S. PATENT DOCUMENTS

| | | |
|---|---|---|
| Re. 33,362 | 10/1990 | Mongeon et al. ......................... 227/19 |
| 3,802,438 | 4/1974 | Wolvek .................................... 128/335 |
| 4,263,903 | 4/1981 | Griggs .................................... 128/92 B |
| 4,278,091 | 7/1981 | Borzone ............................... 128/334 C |
| 4,414,967 | 11/1983 | Shapiro .................................. 128/92 B |
| 4,438,769 | 3/1984 | Pratt et al. ............................ 128/334 R |
| 4,454,875 | 6/1984 | Pratt et al. ............................ 128/92 B |
| 4,527,726 | 7/1985 | Assell et al. .............................. 227/19 |
| 4,586,503 | 5/1986 | Kirsch et al. ............................ 128/334 |
| 4,733,664 | 3/1988 | Kirsch et al. ........................ 128/334 R |

(List continued on next page.)

FOREIGN PATENT DOCUMENTS 0656191   6/1995   European Pat. Off. ...... A61B 17/128

OTHER PUBLICATIONS

Harry S. Soroff, MD, et al., "Improved Sternal Closure Using Steel Bands: Early Experience with Three–Year Follow–up", *Annals of Thoracic Surgery*, vol. 61, pp. 1172–1176, 1996.

Francis Robicsek, MD, et al., "The Prevention and Treatment of Sternum Separation Following Open–Heart Surgery", *The Journal of Thoracic and Cardiovascular Surgery*, pp. 267–268, 1976.

William F. Chlosta, MD, et al., "Simplified Method of Reinforced Sternal Closure", *Annals of Thoracic Surgery*, vol. 60, pp. 1428–1429, 1995.

Samuel L. Kalush, MD, et al., "Peristernal Closure of Median Sternotomy Using Stainless Steel Bands", pp. 172–173, 1975.

Gary Goodman, MD, et al., "Technique of Closure of Median Sternotomy with Trans–sternal Figure–of–Eight Wires", *J. Cardiovasc Surg.*, vol. 27, pp. 512–513, 1986.

Rodman E. Taber, MD, et al., "Prevention of Sternotomy Wound Disruptions by Use of Figure–of–Eight Pericostal Sutures", *Annals of Thoracic Surgery*, vol. 8, No. 4, pp. 267–369, Oct., 1969.

G. Watanabe, et al., "A New Technique of Reinforced Sternal Closure", *Cardiovascular Surgery*, vol. 4, No. 5, pp. 639–640, Oct. 1996.

Yousif D. Al–Naaman, MD, et al., "Sternal Staple: Simple and Rapid Device for Closure of Median Sternotomy", pp. 170–171, 1975.

*Primary Examiner*—Michael Buiz
*Assistant Examiner*—Tina T. D. Pham
*Attorney, Agent, or Firm*—Whitman Breed Abbott & Morgan LLP

[57] ABSTRACT

An improved method of reducing and stabilizing the sternum after a sternotomy includes fixing a staple at the anterior surface of the sternum adjacent to each outlet for trans-sternal wire sutures. The staples are applied to the sternal halves to reinforce the bone adjacent to the suture outlets so as to prevent the suture from cutting into the bone. As each suture loop is tightened to adapt the sternum, the suture loop abuts the staples adjacent the suture outlets. The staples are deformed under force applied by the suture loop to indicate that the loop has been tightened to an optimum degree. A sterile surgical staple gun is employed to install the staples in the sternal halves. A kit for performing the improved sternal reduction procedure includes a pre-sterilized staple gun loaded with surgical staples, as well as suture/needle assemblies.

22 Claims, 7 Drawing Sheets

U.S. PATENT DOCUMENTS

| | | | |
|---|---|---|---|
| 4,896,668 | 1/1990 | Popoff et al. | 606/74 |
| 5,009,663 | 4/1991 | Broome | 606/232 |
| 5,163,598 | 11/1992 | Peters et al. | 227/176 |
| 5,328,077 | 7/1994 | Lou | 227/175 |
| 5,376,101 | 12/1994 | Green et al. | 606/232 |
| 5,381,943 | 1/1995 | Allen et al. | 227/177 |
| 5,395,034 | 3/1995 | Allen et al. | 227/178 |
| 5,411,522 | 5/1995 | Trott | 606/232 |
| 5,423,857 | 6/1995 | Rosenman et al. | 606/219 |
| 5,425,490 | 6/1995 | Goble et al. | 227/175 |
| 5,497,933 | 3/1996 | DeFonzo et al. | 227/175.1 |
| 5,501,696 | 3/1996 | Trott | 606/232 |
| 5,651,491 | 7/1997 | Heaton et al. | 227/175.1 |
| 5,665,109 | 9/1997 | Yoon | 606/232 |
| 5,720,747 | 2/1998 | Burke | 606/74 |
| 5,722,982 | 3/1998 | Ferreira et al. | 606/151 |
| 5,891,168 | 4/1999 | Thal | 606/232 |

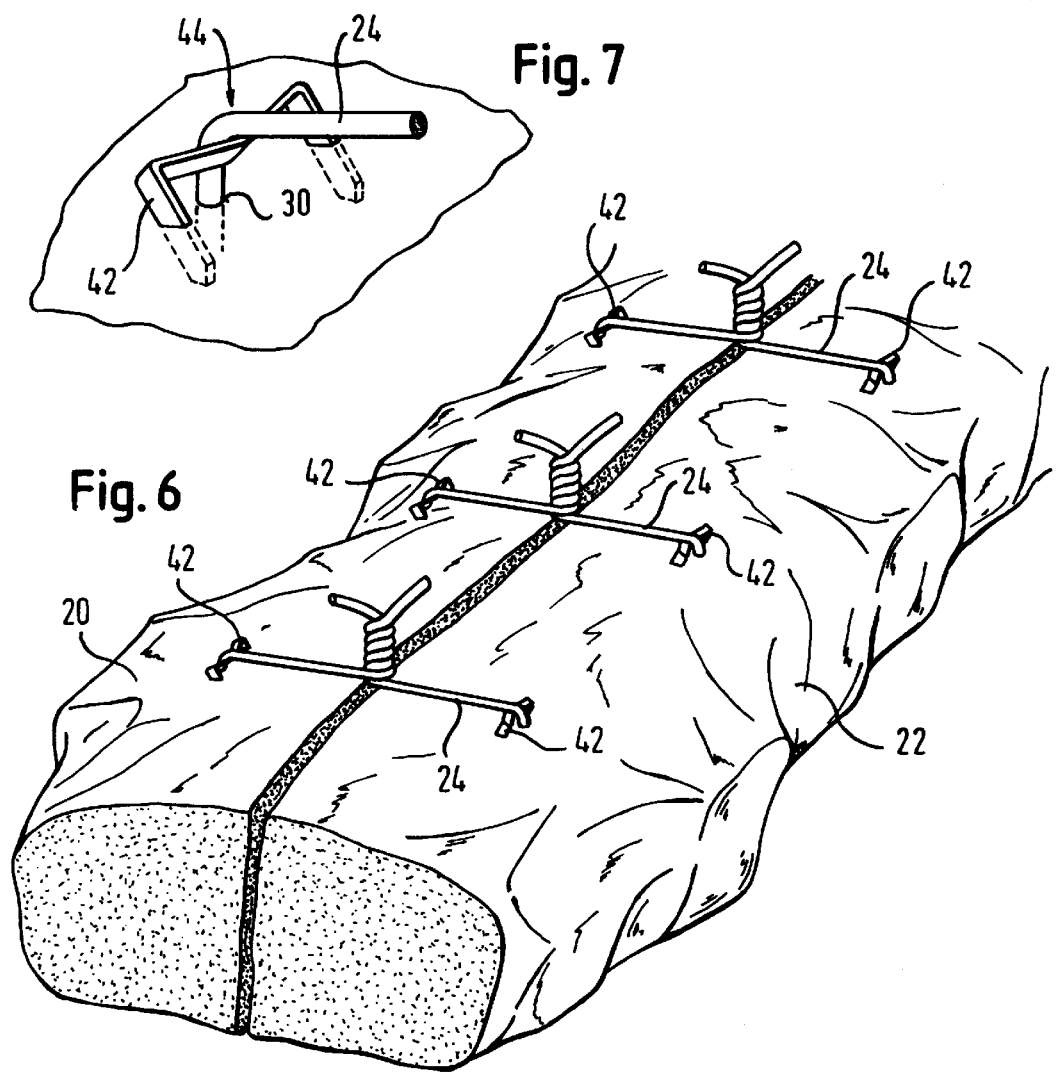
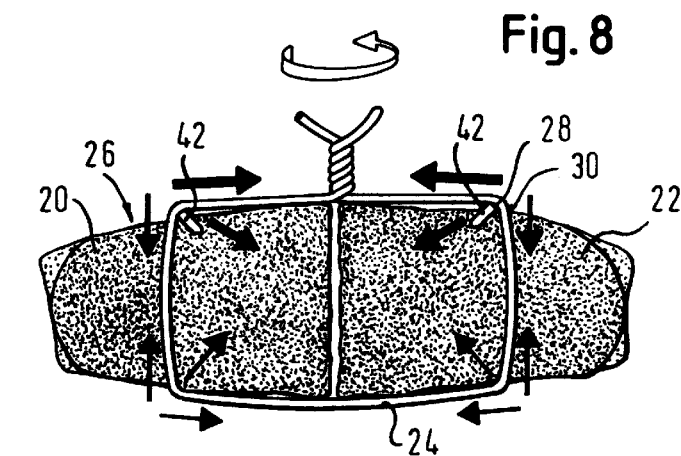

300
STERNAL CLOSURE TECHNIQUE AND KIT FOR PERFORMING SAME

FIELD OF THE INVENTION

This invention relates to a method and apparatus for use during a surgical operation, and more particularly to a method and apparatus for closing the sternum after open-heart surgery.

BACKGROUND OF THE INVENTION

So-called "open-heart" surgical procedures, which include coronary artery bypasses and valve replacements, are among the most commonly performed major operations. These procedures entail splitting the sternum longitudinally and spreading the sternum laterally to provide access to the heart. The latter stages of such procedures include closing and stabilizing the sternum, which is often done by means of wire sutures installed trans-sternally (i.e. through the sternum).

FIG. 1 somewhat schematically illustrates the conventional closure procedure using transsternal sutures. As seen in FIG. 1, split-halves 20 and 22 of the sternum are joined together by a series of wire suture loops 24 spaced at intervals in the longitudinal direction relative to the sternum.

When the quality of the sternal bone is poor, due to osteoporosis or other factors, the wire suture may cut into the split-halves of the sternum as the free ends of the wire sutures are twisted together to draw the sternum together.

FIG. 2 is a view which shows the sternum and one of the suture loops 24 in cross-section. The arrows shown in FIG. 2 indicate the main force vectors which result from twisting the ends of the suture. Most of the tension resulting from the twisting procedure is applied at the anterior surface 26 of the sternum, and particularly at the inner edge 28 of the anterior outlets 30 through which the loop 24 emerges from the bone. If the anterior cortex of the bone is of poor quality, the anterior outlet 30 is cut in an inward direction (i.e. toward the sternotomy and the location where the wire ends are twisted together). Consequently, the wire loop 24 assumes an acute angle configuration at the posterior side of the sternum, as indicated at 32 in FIG. 2. Coughing or other post-operative activity may then cause the acute angles 32 of the wire loop 24 to cut the bone in an inward direction at the posterior side of the sternum, leading to dehiscence (separation) of the sternal halves, as illustrated in FIGS. 3 and 4. Serious complications, including infection, may result from sternal dehiscence.

The problem of sternal dehiscence after closure using suture loops is known to the prior art, and various solutions have been proposed. Among these are reinforcement of the sternum by implantation of longitudinally extending wires, or weaving reinforcement wires around the ribs adjacent to the sternum and then applying sutures peri-sternally (laterally around the sternum) to join the sternal halves. However, these proposed solutions tend to result in increased damage to blood vessels or other soft tissue, and also may substantially increase the time required for closing the chest. Also, if infection occurs, necessitating removal of the sutures, it can be very difficult to remove the reinforcing wires.

Another difficulty encountered in closing the sternum by transsternal sutures is the uncertainty as to whether the suture loops have been tightened to an optimum degree. If the loops are insufficiently tightened, then sternal dehiscence may immediately occur. But if the tightening is excessive, the sternal halves may be cut by the suture, as described above, which also can lead to dehiscence. Because of variations from patient to patient in the mechanical properties of the bone, it is not possible to determine the correct degree of suture loop tension by observing deformation of the bone.

OBJECTS AND SUMMARY OF THE INVENTION

It is accordingly an object of the invention to provide a method of closing the sternum which reduces the risk of sternal dehiscence.

It is a further object of the invention to provide a sternal closure method which can be performed without significantly increasing the length of time required for the procedure.

It is another object to provide a sternal closure method which can be performed with minimal damage to surrounding soft tissue.

It is still a further object of the invention to provide a kit for use in an improved sternal closure technique.

According to an aspect of the invention, there is provided a method of stabilizing the sternum of a patient after surgery in which the sternum is split, the method including the steps of penetrating the anterior surface of the sternum to form an outlet for a suture, fixing a staple in the anterior surface of the sternum adjacent to the outlet, and securing free ends of the suture relative to each other in a manner such that the suture abuts the staple.

Preferably the staple is installed in the anterior surface of the sternum by means of a staple gun.

It is further contemplated that the staple gun be provided as part of a kit which also includes sterilized staples contained in the gun and wire suture/needle assemblies suitable for installing sutures through the sternum.

Staples installed in the sternal halves immediately inwardly from the anterior suture outlets, as provided in accordance with the invention, serve to reinforce the outlets to prevent the sutures from cutting the bone at the anterior side of the sternum. The staples also reduce the risk of the sutures cutting the sternum at its posterior side, thereby maintaining stability of the sternum-halves and preventing sternal dehiscence.

The staples and sutures in the kit are preferably matched to each other in a manner which results in a balance in their mechanical properties. Consequently, as a suture loop is tightened to adapt the sternum, with the suture loop abutting the staples adjacent the suture outlets, force imparted by the tightening suture loop to the staples causes the staples to deform, thereby indicating to the surgeon that the suture loop has been tightened to an optimum degree.

The foregoing and other aspects, features and advantages of the present invention will become more apparent by reference to the appended drawings and the following detailed description of preferred embodiments of the invention.

BRIEF DESCRIPTION OF THE DRAWINGS

FIG. 6 is a perspective view of a sternum closed in accordance with the technique of the present invention.

FIG. 7 shows a detail of the sternal closure of FIG. 6, including a staple in the anterior surface of the sternum and a suture abutting the staple.

FIG. 8 is a sectional view of the sternum closure of FIG. 6.

DETAILED DESCRIPTION OF PREFERRED EMBODIMENTS AND PRACTICES

Figure 1:
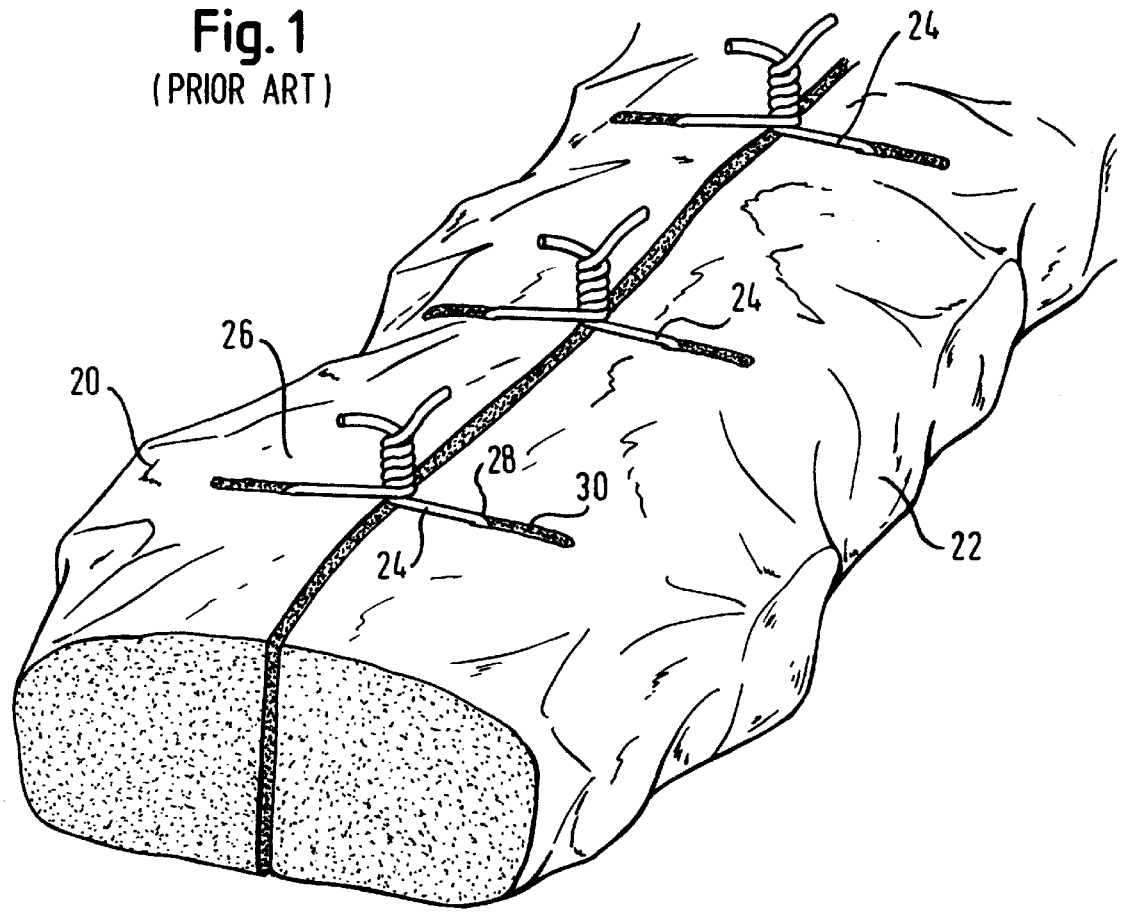
FIG. 1 is a perspective view of a sternum that has been closed in accordance with a conventional surgical technique.
Figure 2:
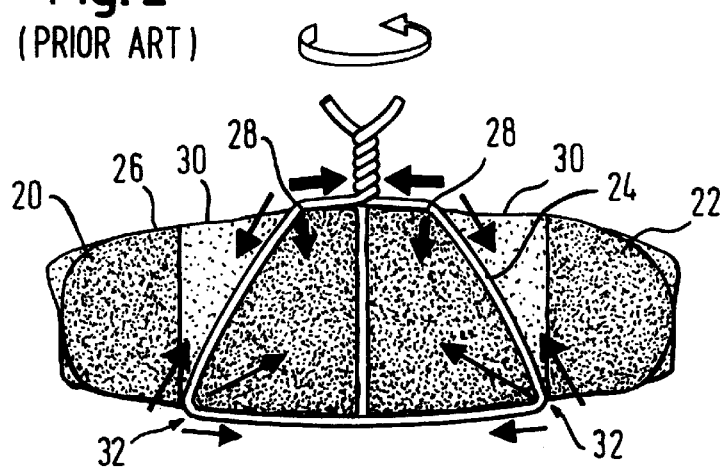
FIG. 2 is a sectional view of the sternum closure of FIG. 1.
Figure 3:
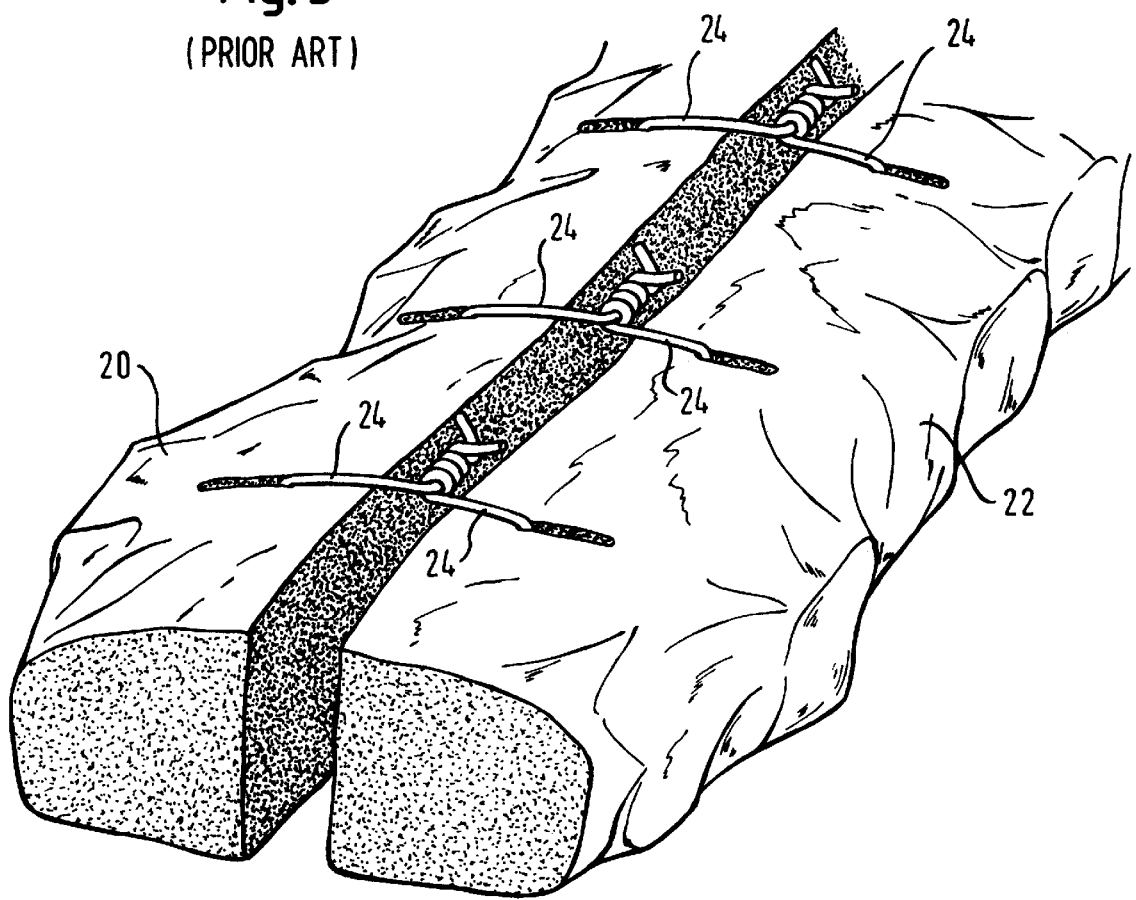
FIG. 3 is a perspective view of the sternum after dehiscence has occurred following the conventional closure technique.
Figure 4:
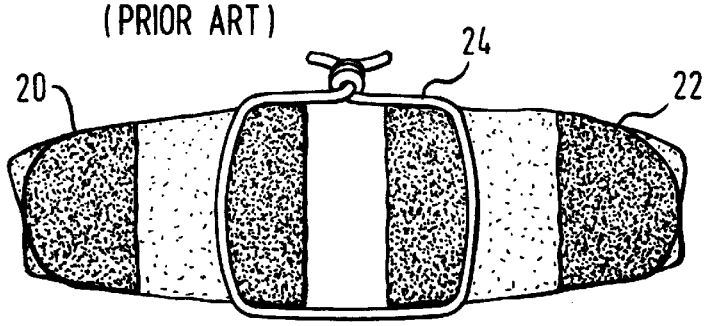
FIG. 4 is a sectional view of the dehiscent condition of FIG. 3.
Figure 5:
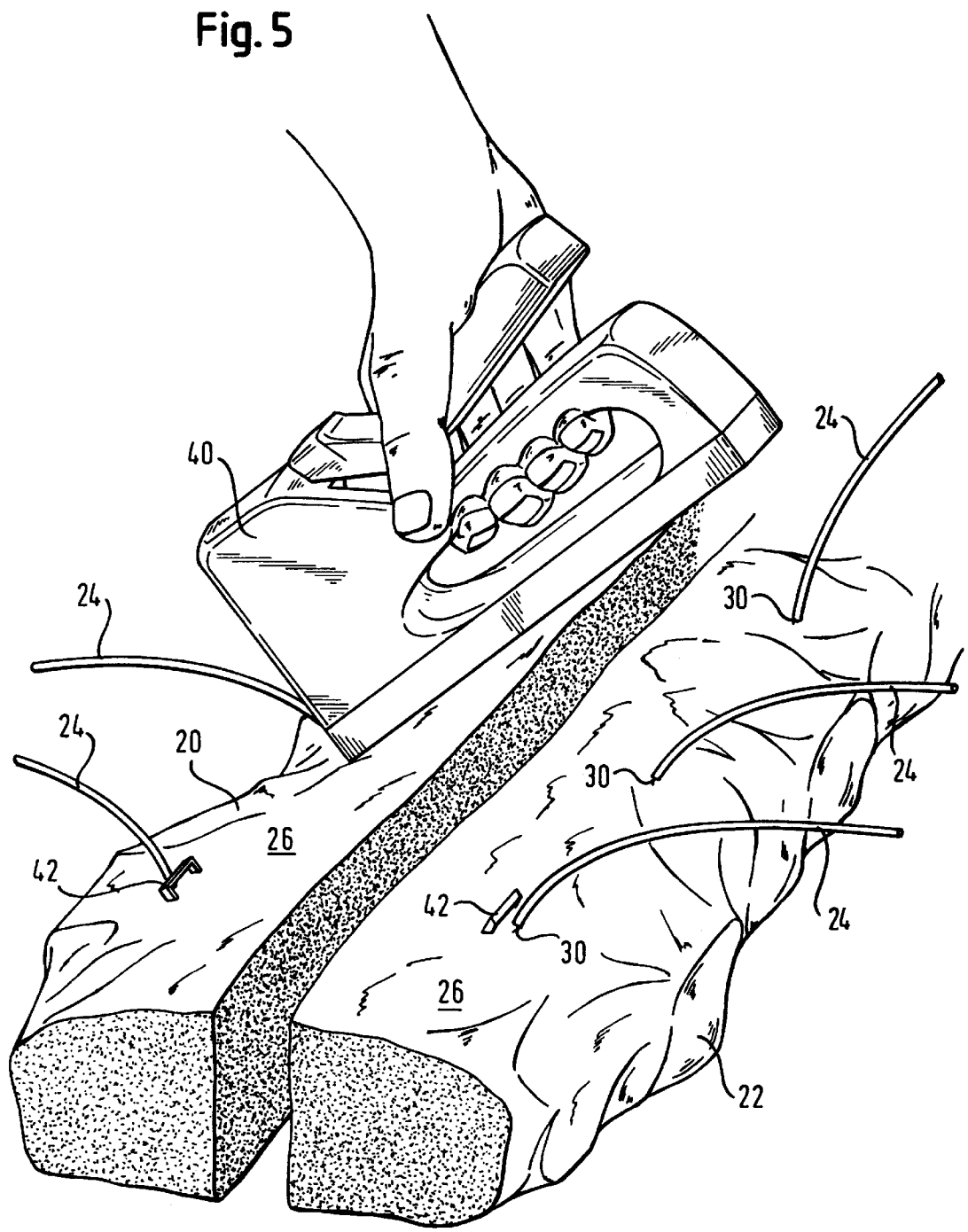
FIG. 5 illustrates installation of staples in sternal halves as part of a sternal closure procedure provided in accordance with the present invention.

The sternal closure technique of the present invention, which includes reinforcement of the sternum with staples preparatory to reducing the sternotomy with trans-sternal wire sutures, will now be described with reference to FIGS. 5–8. FIG. 5, in particular, illustrates the inventive technique. It will be appreciated from FIG. 5 that wire sutures are installed trans-sternally through both split-halves of the sternum. Preferably this is done by a conventional method using a needle (not shown) which is initially attached to an end of the wire suture. With the sutures in place, a staple gun 40 is then used to drive staples 42 into the anterior surface 26 of the sternal halves at points immediately inward (i.e. on the side toward the sternotomy) relative to points of outlet 30 for the wire sutures 24. According to a preferred manner of practicing the invention, and as best seen in FIG. 7, the staples are driven at an angle of substantially 45° relative to the surface 26 of the sternum with the prongs of the staple extending inwardly (toward the sternotomy) and downwardly from the sternal surface. After a respective staple 42 has been driven adjacent to each of the suture outlets 30, the reduction of the sternotomy is completed by the conventional step of twisting the free ends of each suture together to form a loop and to draw the sternal halves together.

The staples 42 are preferably designed to deform to a modest extent at the back portions of the staples in response to a force imparted to the back of the staple by a predetermined degree of tension in the suture 24. The deformation of the back of the staple is indicated at 44 in FIG. 7. The amount of force required to deform the back of the staple so as to bow it downwardly by a distance substantially corresponding to the cross-sectional diameter D of the suture 24 is preferably on the order of 40 to 800 N. A preferred value for the force required to bow the staple back by the distance D is 200 N. The deformation of the back of the staple provides to the surgeon a visual cue to indicate that the twisting of the ends of the sutures has brought the suture loop into a condition that is tight enough, but not too tight, so as to minimize the risk of sternal dehiscence.

FIGS. 6 and 8 illustrate the sternal closure obtained when the suture loops have been tightened to an optimum degree. The staples 42 serve to reinforce the inward edges of the anterior outlets 30 of the suture loops 24, thereby helping to prevent cutting of the bone tissue by the suture at the anterior surface of the sternum. Consequently, the angle formed by the suture loop 24 at the posterior of the sternum is maintained at substantially 90° or more. Moreover, the frictional force applied by the staples 42 to the suture loop helps to reduce the force applied by the suture loop at the posterior side of the sternum. As a result, cutting into the bone at the posterior side of the sternum is also prevented. In vitro testing has indicated that the installation of reinforcing staples at the anterior side of the sternum will serve to reduce the risk of dehiscence relative to the conventional trans-sternal suture closure technique which does not employ reinforcement. The installation of the staples may be accomplished in a minimal amount of time by using the staple gun and does not entail damage to surrounding tissue. Further, if removal of the sutures becomes necessary post-operatively, the staples would not impede removal, and can easily be removed themselves at the same time.

Figure 9:
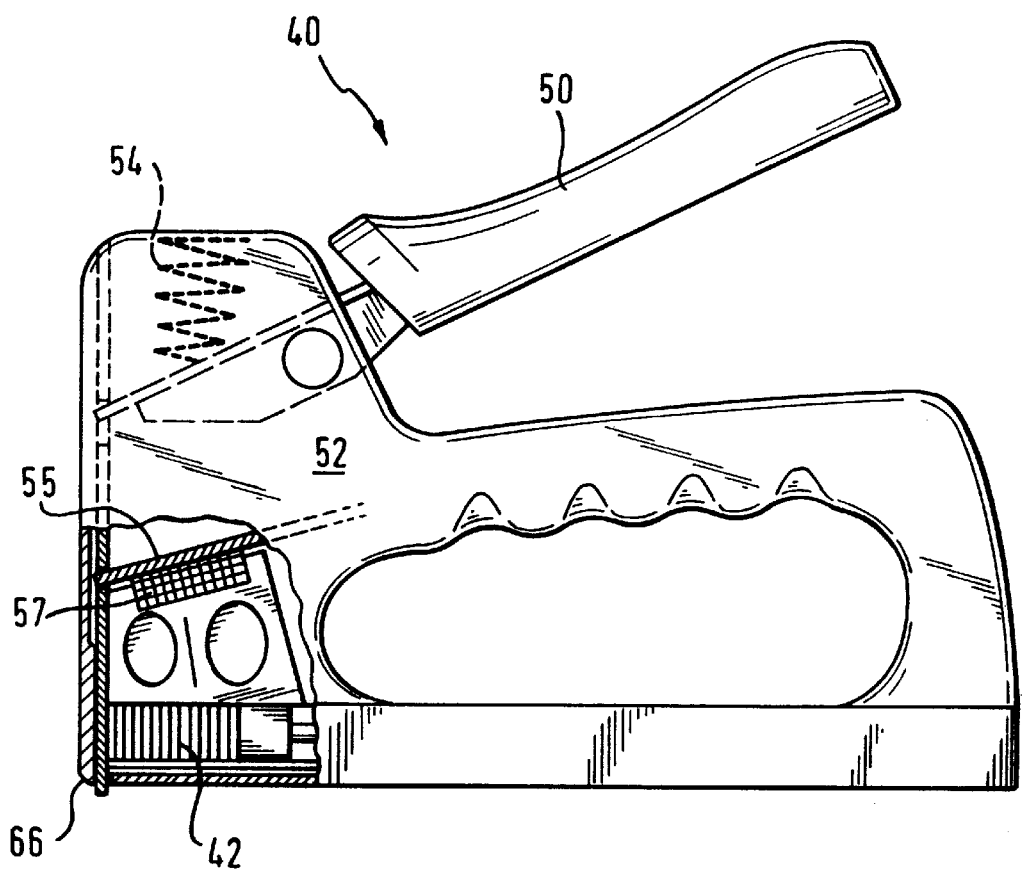
FIG. 9 is a somewhat schematic side view of a staple gun provided in accordance with the invention, with a portion of the gun housing broken away.
Figure 10:
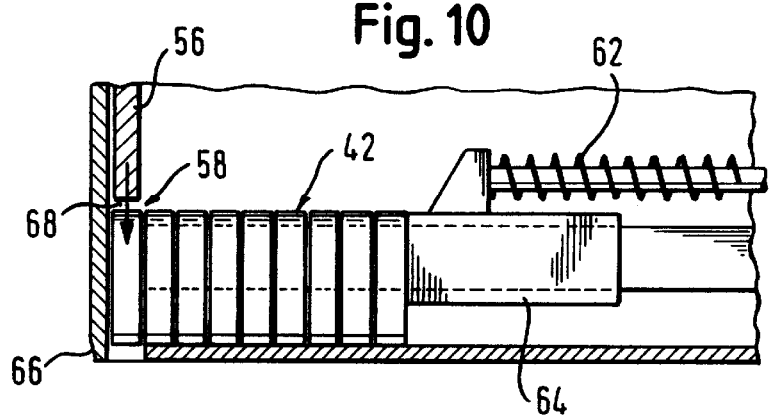
FIG. 10 is a more detailed side view, with the housing removed, of a portion of the staple gun of FIG. 9, showing a staple transport channel.
Figure 11:
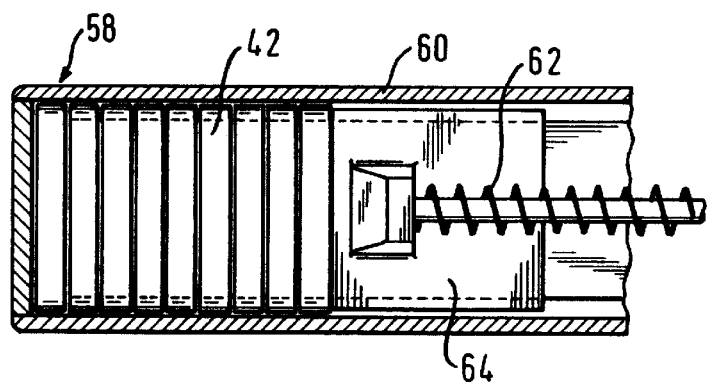
FIG. 11 is a plan view of the staple transport channel of FIG. 10.

FIGS. 9–11 illustrate features of a staple gun 40 provided in accordance with the invention for the purpose of installing staples 42 in the sternal halves. A preferred embodiment of the staple gun 40 is adapted from a commercially available staple gun/tacker used for industrial or construction applications. Mechanically, the preferred surgical staple gun 40 operates in a manner identical to that of the commercial staple gun, but the materials used to make at least some of the components of the commercial gun are changed so as to be suitable for use in a surgical device.

Referring to FIG. 9, the operating mechanism of the staple gun 40 includes, as in a conventional design, a lever 50 which may be squeezed downwardly by the surgeon relative to the main housing 52 of the staple gun to compress a spiral spring 54 and to charge a leaf spring 55. At a certain point the spring 54 is released to drive a striking member or hammer 56. The hammer 56 is driven downwardly to strike the back of a staple 42 present at a driving position 58, so that the staple 42 is driven into the sternum. A mechanical stop 57 for the leaf spring 55 limits the downward stroke of the hammer and therefore also limits the distance that the staple 42 is driven into the sternum.

A series of staples 42 are contained in a channel 60 within the housing 52 of the staple gun 40. A spring 62 biases a pushing element 64 to push the series of staples 42 towards the driving position 58.

The components of the staple gun 40 should be made of materials suitable for undergoing conventional surgical instrument sterilization procedures. No grease or other lubricant should be included in the staple gun. The staple gun should be free of pyrogenic material and, prior to use, should be treated so as to have a low bio-burden.

If the housing 52 is formed of plastic, it should be of a type which can be irradiated without loss of mechanical properties. The channel 60 for the staples should be formed of stainless steel or coated with a biocompatible material, instead of the chrome-plated steel frequently used in industrial staple guns. A nose portion 66 of the staple gun, adjacent to the driving position 58 for the staples, should be made of a biocompatible material suitable for contact with the patient.

It will be recognized that the staples 42 also should be formed of a biocompatible material. One suitable material is the well-known metal composition available under the trademark "PHYNOX®". It is also contemplated to use another known biocompatible metal composition, or a suitable plastic composition. Biocompatibility for the staples may also be achieved by applying a suitable coating.

It is desirable that the staples 42 be formed of a material which is electrically compatible with the material of the sutures, so that electro-corrosion does not develop post-operatively. In a preferred embodiment of the invention, electrical compatibility is assured by forming both the sutures and the staples of the same material, such as PHYNOX. It is also desirable that the hammer 56 of the staple gun 40 be formed of a material that is both biocompatible and electrically compatible with the staples, or that a bottom (striking) end 68 of the hammer 56 (see FIG. 5) be coated with compatible material. In either case, it will be appreciated that the striking surface of the hammer 56 (i.e. the surface which strikes the staples) would be formed of a biocompatible material. Assuming that PHYNOX staples are to be employed, the bottom end 68 of the hammer may be coated with or formed of PHYNOX. This precaution should be taken because small particles from the bottom end of the hammer may be implanted in the staple when the hammer strikes the staple.

Insertion of the staples 42 into the channel 60 of the staple gun prior to use calls for loading of the staples one by one, presumably by hand. It is not feasible under present circumstances to glue the staples 42 together and to load the staples en masse, because no suitable medically-approved adhesive is available for that purpose. Currently available surgical adhesives would not permit the staple at the driving position, if glued to other staples, to be properly separated from its mates upon striking by the hammer 56.

Figure 12:
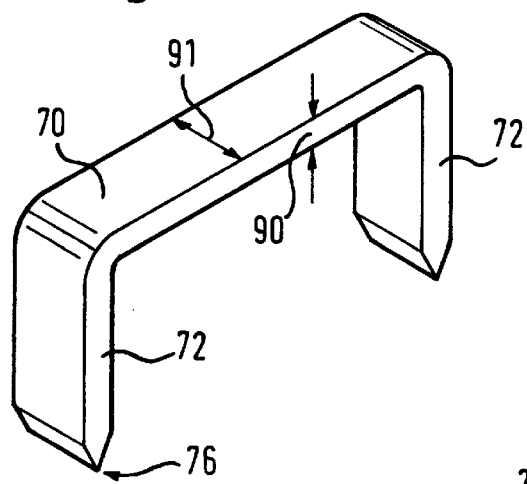
FIGS. 12 and 13 respectively show embodiments of a staple suitable for use with the staple gun of FIG. 9.
Figure 13:
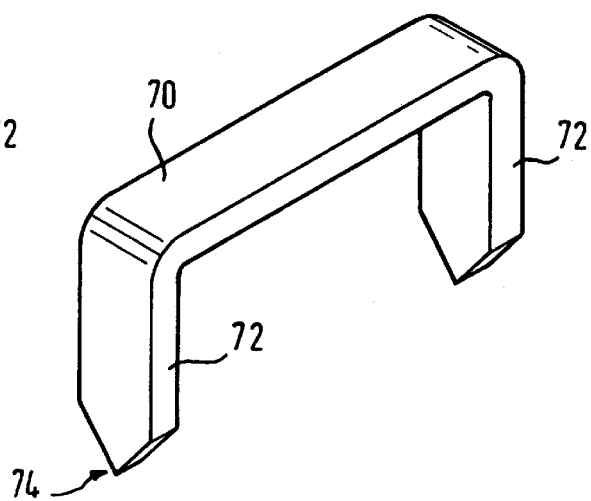

The geometric configuration of the staples 42 may comport with that of conventional office or industrial staples. FIGS. 12 and 13 respectively illustrate suitable configurations. In each case the staple includes a back portion 70 joining two prongs 72. The tip of each prong is pointed in a "V" configuration either at the outside of the prong (as indicated at 74 in FIG. 13), or laterally relative to the prong (indicated at 76 in FIG. 12). It is preferable that the points of the staple prongs be symmetrical about a central plane of the prong, as is the case in the point configurations 74 and 76 shown in the drawings, because the symmetrical point more evenly distributes stress within the bone tissue.

It is notable that the present invention departs from previous proposals for bone-stapling with a staple gun (as in U.S. Pat. Nos. 4,414,967 and 5,163,598) in that the present invention contemplates using a staple gun to drive both prongs of the staple into a single continuous piece of bone. By contrast, prior art bone staplers have been employed to drive respective prongs of a staple into two separate bone pieces so as to stabilize the bone pieces with respect to each other. Also, prior art use of staples has called for driving the prongs in a direction normal to the bone surface, rather than at the 4520 angle disclosed herein.

It is contemplated that the concept of driving a staple into a continuous piece of bone as a reinforcement in support of adjacent sutures or other structure may find application in other procedures in addition to sternal closure.

Figure 14:
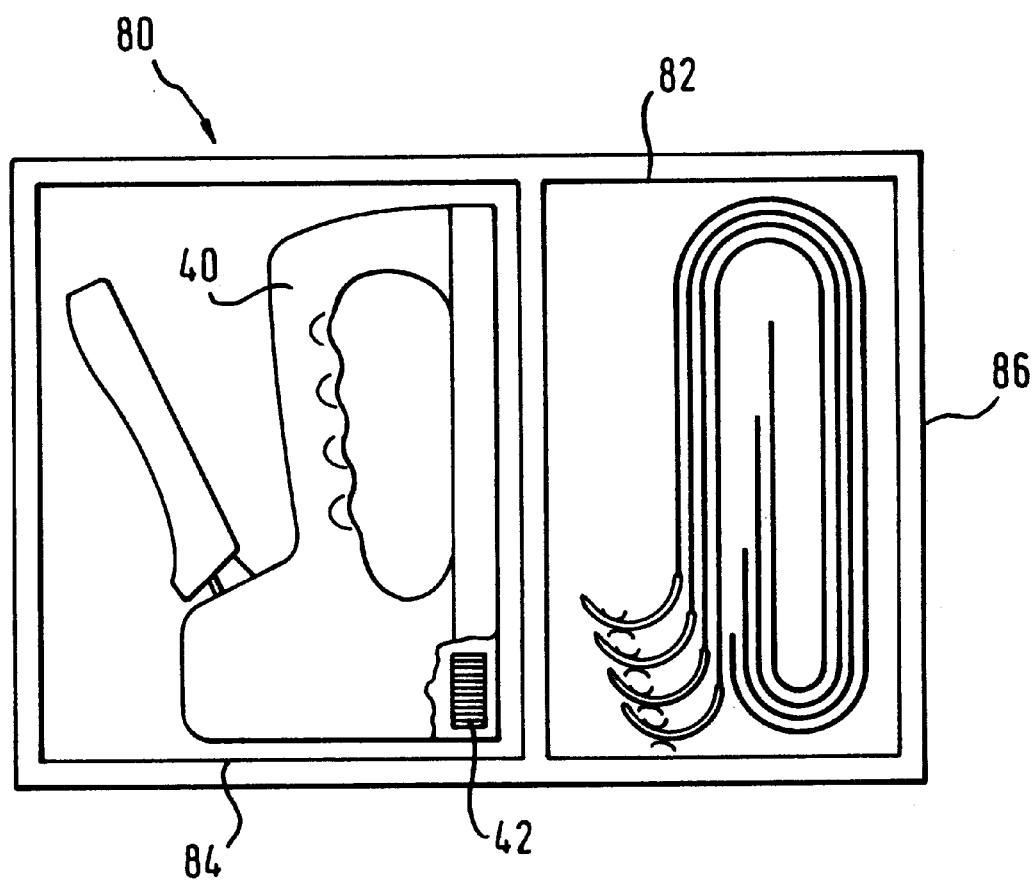
FIG. 14 is a schematic illustration of a kit provided in accordance with the invention for performing the sternum closing technique shown in FIG. 5.

The present invention also contemplates providing a kit containing materials and implements ready for use in the sternal closure technique disclosed above. Such a kit is schematically illustrated in FIG. 14 and indicated generally by reference numeral 80. The major components of the kit 80 are (a) a staple gun 40 loaded with staples 42, both as described above; and (b) a number of suture/needle assemblies 82, which may be like those employed in the conventional technique for adapting the sternotomy by trans-sternal suturing. It should be understood that the staple gun 40 and staples 42 are to be pre-sterilized and packaged within a sterile and protective enclosure, such as a sterile bubble-pack schematically indicated at 84 in FIG. 14. Preferably, the number of sutures is four, six or eight with the suitable number to be selected depending on the size of the patient. It will be appreciated that the number of staples 42 in the staple gun 40 should be at least twice the number of associated suture/needle assemblies.

The packaged staple gun 40 and suture/needle assemblies 82 may all be combined within a single outer packaging structure (schematically illustrated at 86) to form the kit 80. Alternatively, the kit 80 may be assembled in the form of separate packages respectively incorporating the staple gun 40 and one or more of the suture/needle assemblies 82.

Provision of staples and wire suture material together in the same kit makes it possible to assure that the staples and sutures are electrically and mechanically compatible with each other.

The mechanical properties of the staples and the wire sutures are to a considerable extent a function of their geometry and dimensions. Preferred dimensioning and other characteristics of the staples and wire sutures will now be described.

As noted before, the wire sutures preferably conform to conventionally-employed wire sutures, and thus have a substantially circular cross-section. The cross-sectional diameter D of the wire sutures may be in the range 0.4 to 2.0 mm, and 0.9 mm is a preferred value. The ultimate tensile strength (UTS) of the wire sutures may be in the range 400 to 1800 N/mm$^2$; and their yield strength (YS) may be in the range 250 to 1100 N/mm. A preferred specimen of PHYNOX wire suture exhibits UTS=850 N/mm$^2$ and YS=500 N/mm$^2$.

The staples 42 are preferably formed of wire stock having a substantially rectangular cross-section so that the back 70 of the staple exhibits a width W (indicated at 91 in FIG. 12) and a thickness T (indicated at 90). Satisfactory ranges of dimensions of W and T are 0.6 to 5.0 mm and 0.2 to 2.0 mm, respectively. A preferred staple, formed of PHYNOX, has W=1.4 mm and T=0.6 mm. The length of the back 70 of the staple is preferably in the range 5 mm to 30 mm, with a particularly preferred length being 12 mm. Of course, these dimensions may be altered without departing from the invention.

The ultimate tensile strength of the wire stock of which the staple is formed may be in the range 1,000 to 2,800 N/mm$^2$ and the yield strength may be in the range 500 to 1,400 N/mm$^2$. The wire stock employed in a preferred embodiment of the staple exhibits UTS=1,600 N/mm$^2$ and YS=900 N/mm$^2$.

To achieve preferred mechanical interaction between the wire sutures and the staples, including deformation of the staples when optimum tightening of the suture has occurred, an aspect of the present invention calls for certain preferred relationships between the dimensions and mechanical characteristics of the staples and wire sutures. It is preferred that the above defined cross-sectional dimensions be related by:

(a) W>D>T; and
(b) the cross-sectional area of staple back 70 (=W·T) should be less than three times the cross-sectional area of the wire suture (the wire cross-section is given by $\pi \cdot D^2/4$).

Moreover, the ultimate tensile strength of the staple should exceed the UTS of the wire suture, and the yield strength of the staple should exceed the YS of the wire suture.

Providing the staples and the sutures with mechanical characteristics such that the staples deform to indicate an optimum degree of tension in the sutures is a significant aid to the surgeon, and helps to assure that the sternal closure is performed satisfactorily and sternal dehiscence is prevented.

It is to be understood that the above description may indicate to those skilled in the art additional ways in which the principles of this invention may be used without departing from the spirit of the invention. The particularly preferred methods and apparatus are thus intended in an illustrative and not limiting sense. The true spirit and scope of the invention are set forth in the following claims.

What is claimed is:

1. A sternum closure kit, comprising in combination:

a plurality of staples for being driven into split-halves of a sternum; and a plurality of wire sutures for being installed transsternally, said sutures having a cross-sectional diameter D;

said staples each having a back portion and a pair of prongs, each of said prongs extending downwardly from a respective end of said back portion, each of said prongs extending in a respective direction, said directions being substantially parallel to each other, each of said prongs terminating in a respective pointed end, said staples being formed such that a force in the range 40 to 800 N applied downwardly at a central point of said back portion causes said back portion to bow downwardly by a distance substantially equal to D.

2. A sternum closure kit according to claim 1, wherein said back portion of said staple has a substantially rectangular cross-section having a width W and a thickness T, with $W>D>T$ and $W\cdot T<3\cdot\pi\cdot D^2/4$.

3. A sternum closure kit according to claim 1, wherein said staples are formed of a wire stock material having an ultimate tensile strength (UTS) greater than the UTS of said sutures.

4. A sternum closure kit according to claim 1, wherein said staples are formed of a wire stock having a yield strength (YS) greater than the YS of said sutures.

5. A sternum closure kit according to claim 1, further comprising a staple gun in which said staples are loaded.

6. A sternum closure kit according to claim 1, wherein each of said wire sutures has a needle attached at one end of the suture.

7. A sternum closure kit according to claim 1, wherein the back portion of each of said staples is substantially straight.

8. A sternum closure kit, comprising in combination:

a sterilized staple gun containing a plurality of sterilized staples; and a plurality of sterilized suture and needle assemblies;

wherein said staples are separate from said suture and needle assemblies.

9. A sternum closure kit according to claim 8, wherein said staples are formed of a biocompatible material that is the same as a material of which the sutures are formed.

10. A sternum closure kit according to claim 9 wherein said sutures and said staples are formed of metal.

11. A sternum closure kit according to claim 7, wherein said staples and said sutures are formed of respective metal wire stock materials, said sutures having a substantially circular cross-section with a diameter D, said staples having a substantially rectangular cross-section having a width W and a thickness T, with $W>D>T$ and $W\cdot T<3\cdot\pi\cdot D^2/4$.

12. A sternum closure kit according to claim 8, wherein said staples are formed of a wire stock material having an ultimate tensile strength (UTS) greater than the UTS of said sutures.

13. A sternum closure kit according to claim 8, wherein said staples are formed of a wire stock having a yield strength (YS) greater than the YS of said sutures.

14. A sternum closure kit according to claim 8, wherein said plurality of staples includes at least twice as many staples as the number of suture and needle assemblies in said kit.

15. A method of stabilizing the sternum of a patient after surgery in which the sternum is split, the method comprising the steps of:

penetrating the anterior surface of the sternum to form an outlet for a suture;

fixing a staple in the anterior surface of the sternum adjacent to said outlet; and securing free ends of said suture relative to each other in a manner such that said suture abuts said staple.

16. A method according to claim 15, wherein said securing step includes twisting together the free ends of said suture until said staple is deformed by force imparted to said staple by said suture.

17. A method according to claim 15, wherein said staple has prongs which are driven into the sternum at substantially a 45° angle relative to the anterior surface of the sternum.

18. A method according to claim 15, wherein said staple is made of a biocompatible material that is the same as a material of which the suture is formed.

19. A method according to claim 18, wherein said staple and said suture are formed of respective metal wire stock materials, said suture having a substantially circular cross-section with a diameter D, said staple having a substantially rectangular cross-section having a width W and a thickness T, with $W>D>T$ and $W\cdot T<3\cdot\pi\cdot D^2/4$.

20. A method according to claim 15, wherein said staple is formed of a wire stock material having an ultimate tensile strength (UTS) greater than the UTS of said suture.

21. A method according to claim 15, wherein said staple is formed of a wire stock having a yield strength (YS) greater than the YS of said suture.

22. A method according to claim 15, wherein said fixing step includes driving the staple into the sternum by using a staple gun.

* * * * *